United States Patent [19]

Imai

[11] 4,356,334
[45] * Oct. 26, 1982

[54] SYNTHESIS OF ALCOHOLS

[75] Inventor: Tamotsu Imai, Mount Prospect, Ill.

[73] Assignee: UOP Inc., Des Plaines, Ill.

[*] Notice: The portion of the term of this patent subsequent to Dec. 18, 1996, has been disclaimed.

[21] Appl. No.: 236,430

[22] Filed: Feb. 20, 1981

Related U.S. Application Data

[63] Continuation-in-part of Ser. No. 113,880, Jan. 21, 1980, abandoned, which is a continuation-in-part of Ser. No. 39,633, May 16, 1979, abandoned.

[51] Int. Cl.$^3$ .............................................. C07C 27/22
[52] U.S. Cl. ..................................... 568/909; 564/467
[58] Field of Search .......................... 564/467; 568/909

[56] References Cited

U.S. PATENT DOCUMENTS

| | | | |
|---|---|---|---|
| 2,497,310 | 2/1950 | Larson | 260/585 |
| 4,179,469 | 12/1979 | Imai | 564/467 |
| 4,250,115 | 2/1981 | Imai | 564/467 |

*Primary Examiner*—Joseph E. Evans
*Attorney, Agent, or Firm*—James R. Hoatson, Jr.; Raymond H. Nelson; William H. Page, II

[57] ABSTRACT

Alcohols may be synthesized by reacting an olefinic hydrocarbon, carbon monoxide, and hydrogen in the presence of a catalyst comprising a rhodium carbonyl or organohodium complex and a promoter comprising ammonia at temperatures in the range of from about 50° to about 250° C. and a pressure in the range of from about 10 to about 300 atmospheres to produce the desired alcohol.

11 Claims, No Drawings

SYNTHESIS OF ALCOHOLS

CROSS-REFERENCE TO RELATED APPLICATIONS

This application is a continuation-in-part of my co-pending application, Ser. No. 113,880 filed Jan. 21, 1980, and now abandoned which is a continuation-in-part of my co-pending application, Ser. No. 39,633 filed May 16, 1979 and now abandoned, all teachings of which are icorporated herein by reference thereto.

BACKGROUND OF THE INVENTION

Heretofore, it has been known to prepare alcohols from unsaturated hydrocarbons utilizing an oxo process. Conventional catalysts for this process have comprised cobalt complex catalysts. For example, U.S. Pat. No. 3,278,612 discloses a process for obtaining alcohols utilizing olefinic hydrocarbons as the starting material. These olefinic hydrocarbons are treated or reacted with carbon monoxide and hydrogen at elevated temperature and pressure in the presence of a catalyst consisting essentially of a cobalt complex compound along with an organophosphine and an inorganic basic compound. Examples of these catalysts which are disclosed in the patents include cobalt carbonyl as well as phosphines such as triethyl phosphine, tri-n-butyl phosphine, tricyclohexyl phosphine etc. This patent teaches that, in view of the fact that cobalt carbonyl loses its catalytic activity when the reaction system is effected in an alkaline medium, it is necessary to have an organophosphine ligand present. As will hereinafter be more fully discussed, the presence of such a ligand in the process of the present invention will afford a deleterious effect.

Another U.S. Patent, namely U.S. Pat. No. 2,497,310, dicloses a method for synthesizing amine compounds. In this process, an unsaturated hydrocarbon is reacted with carbon monoxide, hydrogen and ammonium to produce nitrogen-containing organic compounds, and particularly amines. The reaction is catalyzed by catalysts which are known to be effective in other hydrogenation reactions, such as cobalt, nickel, ruthenium, iron, copper, etc. However, in this patent, the ammonia or substituted ammonias are essential reactants for the process, thus differing from the process of the present invention.

This invention relates to a process for the synthesis of alcohols. More specifically, the invention is concerned with a process for synthesizing alcohols, and specifically primary alcohols, by reacting olefinic hydrocarbons, carbon monoxide and hydrogen in the presence of certain catalytic compositions of matter as well as a promoter compound.

It is well known in the chemical art that alcohols constitute an important class of compounds. For example, relatively long chain primary alcohols such as n-dodecanol (lauryl alcohol) is an important intermediate in the preparation of synthetic detergents as well as lube additives, pharmaceuticals, rubber, textiles and perfumes. Likewise, n-tetradecanol (myristyl alcohol) is a useful intermediate in the preparation of plasticizers as well as being used as an antifoam agent, an intermediate in the preparation of perfume fixatives for soaps and cosmetics, etc. Lower molecular weight alcohols such as butanol are utilized by the preparation of esters such as butyl acetate, as a solvent for resins and coatings, as well as being used in plasticizers, detergent formulations, dehydrating agents, hydraulic fluids, etc.

It is therefore an object of this invention to provide a prpcess for the synthesis of alcohols.

A further object of this invention is to provide a process for synthesizing alcohols utilizing relatively inexpensive starting materials, said process being effective in the presence of certain catalysts and a promoter.

In one aspect, an embodiment of this invention resides in a process for the synthesis of an alcohol by the reaction of an olefinic hydrocarbon, carbon monoxide, and hydrogen in the presence of a catalyst selected from the group consisting of rhodium carbonyl compounds and rhodiumorganometallic compounds, at reaction conditions, and recovering the resultant alcohol, the improvement which comprises utilizing an aqueous solution of ammonia as a promoter to produce alcohol as the major product of the process.

A specific embodiment of this invention is found in a process for the synthesis of an alcohol which comprises reacting undecene, carbon monoxide and hydrogen in the presence of chlorodicarbonylrhodium dimer and aqueous ammonia at a temperature in the range of from about 50° to about 250° C. and a pressure in the range of from about 10 to about 300 atmospheres, and recovering the resultant dodecanol.

Other objects and embodiments will be found in the following further detailed description of the present invention.

As hereinbefore set forth, the present invention is concerned with a process for the synthesis of alcohols in which an olefinic hydrocarbon is reacted with carbon monoxide and hydrogen in the presence of certain catalytic compositions of matter and promoters comprising ammonia. By utilizing a catalyst of the type hereinafter set forth in greater detail, that is, a compound containing rhodium along with the promoter, it is possible to obtain the desired alcohols without the necessity of having other extraneous materials present in the reaction mixture, these extraneous materials being susceptible to entering into the reaction and thus affording unwanted side products.

The reaction conditions which are employed to produce the desired results will include a temperature in the range of from about 50° to about 250° C. and pressures within the range of from about 10 to about 300 atmospheres. In the preferred embodiment of the invention, the pressures which are employed to effect the desired results will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 2000:1 moles of olefin per mole of catalyst and a mole ratio of ammonia to catalyst in the range of from about 50:1 to about 300:1 moles of ammonia per mole of catalyst.

Examples of olefinic hydrocarbons which may be employed to effect the process of this invention will include straight chain olefins containing from 3 to about 30 carbon atoms such as propylene, butene-1, butene-2, pentene-1, pentene-2, hexene-1, hexene-2, hexene-3, heptene-1, heptene-2, heptene-3, octene-1, octene-2, octene-3, octene-4, nonene-1, nonene-2, nonene-3, nonene-4, as well as the isomeric decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, octacosenes, nonacosenes, triacontenes, etc.

The reaction between the hydrocarbons of the type hereinbefore set forth, carbon monoxide and hydrogen is effected in the presence of a catalyst comprising a rhodium carbonyl compound or an organorhodium complex. Examples of specific catalysts which may be employed will include rhodium nitrate, rhodium chloride, rhodium bromide, rhodium iodide, rhodium fluoride, chlorodicarbonylrhodium dimer, rhodium carbonyl, chlorobis (ethylene) rhodium dimer, hexarhodium-hexadecacarbonyl, tetrarhodium-dodecacarbonyl, rhodium acetate, rhodium acetylacetonate, rhodium formate, rhodium propionate, rhodium butyrate, etc. It is to be understood that when the rhodium compounds comprise the nitrates or halides as the starting compound, a rhodium carbonyl complex will be formed under the reaction conditions which are employed in the process. It is to be understood that the aforementioned rhodium compounds are only representative of the class of compounds which may be employed, and that the present invention is not necessarily limited thereto. However, organorhodium complexes having phosphorus-containing ligands are excluded since alcohol formation is suppressed by phosphorus-containing ligands and aldehyde formation is increased.

In addition to utilizing a catalyst of the type hereinbefore set forth in greater detail, the reaction between olefinic hydrocarbon, carbon monoxide and hydrogen is also effected in the presence of a promoter comprising ammonia. The ammonia which is utilized as the promoting agent in the process of this invention may be used in either gaseous, liquefied or aqueous form, depending to some extent on the reaction parameters of temperature and pressure which are employed. When utilizing ammonia as an aqueous solution, the ammonia may be present in a range of from about 10% to about 95% or more, the preferred amount being about 30% by weight of the solution or more.

The process of this invention may be effected in any suitable manner and may comprise either a batch or continuous type of operation. When a batch type of operation is used, a quantity of the olefinic hydrocarbon, the rhodium carbonyl compound or the rhodium metallic complex catalyst and the ammonia promoter in an appropriate form such as an aqueous solution, are charged to an appropriate pressure resistant apparatus such as an autoclave of the rotating, rocking or mixing type. After placing the components of the reaction in the autoclave, it is then sealed and hydrogen and carbon monoxide are charged thereto until the desired operating pressure has been attained. Alternatively, as hereinbefore discussed, if higher pressures are to be employed, a portion of the pressure may be afforded by the introduction of a substantially inert gas into the reaction zone. After reaching the proper operating pressure, the apparatus is then heated to the desired operating temperature which may range from about 50° to about 250° C. and maintained thereat for a predetermined residence time which may range from about 0.1 hour up to about 10 hours or more in duration. Upon completion of the desired residence time, heating is discontinued and the apparatus and contents thereof are allowed to return to room temperature. Upon reaching room temperature, the pressure is discharged, the apparatus is opened and the reaction mixture is recovered therefrom. After separation from the catalyst, the reaction mixture may be subjected to conventional means of separation whereby the desired alcohol is separated from any unreacted starting material, promoter and/or unwanted side reaction products which may have formed, and recovered. A particular advantage which may be obtained when utilizing the process of the present invention is that the catalysts which are employed to effect the reaction are easily recovered as distillation bottom products and may be recycled for reuse. In addition, another advantage which is present is that the loss of products in the distillation step is very low inasmuch as alcohols do not polymerize readily and may therefore be recovered in an excellent yield.

It is also contemplated within the scope of this invention that the synthesis of alcohols may be accomplished by utilizing a continuous method of operation. When utilizing this type of operation, the olefinic hydrocarbon is continuously charged to a reaction zone which is maintained at the proper operating conditions of temperature and pressure and which contains a catalyst of the type hereinbefore set forth as well as the ammonia promoter. Alternatively, the ammonia promoter may also be continuously charged to the reaction zone either separately or along with the olefinic hydrocarbon charge. In addition to the continuous charging of the reactant to the operating zone, hydrogen and carbon monoxide either separately or in admixture are also charged thereto. Upon completion of the desired residence time in the reaction zone, the reactor effluent is continuously withdrawn and subjected to conventional means of separation, such as fractional distillation, whereby the desired alcohol is separated from unreacted starting materials and/or undesired side reaction products which may have formed, and recovered, while the unreacted starting materials may be recycled to the reaction zone to form a portion of the feedstock.

Examples of alcohols which may be synthesized according to the process of the present invention will include primary alcohols such as butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, etc.

The following examples are given to illustrate the process of the present invention. However, it is to be understood that these examples are given merely for purposes of illustration and that the present invention is not necessarily limited thereto.

EXAMPLE I

In this example, 0.0291 grams of a catalyst comprising chlorodicarbonylrhodium dimer was placed in the glass liner of a rotating autoclave. In addition, 30.03 grams of undecene and 0.406 grams of ammonia in the form of a 29.91 wt. % aqueous ammonia solution (1.5cc) was also placed in the autoclave. The autoclave was then sealed and a 1:1 mixture of carbon monoxide and hydrogen was charged to the autoclave until 150 atmospheres of the blend gas had been added. The mole ratio of undecene to rhodium was 1176:1 and the mole ratio of ammonia to rhodium was 165:1. The autoclave was then heated to a temperature of 150° C. and maintained in a range of from 150° to 152° C. for a period of 3 hours, the operating pressure during this time being 176 atmospheres. At the end of the 3 hour period, heating was discontinued and the autoclave was allowed to return to room temperature. Upon reaching room temperature, the excess pressure was discharged and the reaction mixture was recovered from the autoclave. Analysis of the product by means of gas liquid chromatography and elementary analysis disclosed that there had been a 100% conversion of the olefin with a 54.3% selectivity to the alcohol, dodecanol, a 3.7% selectivity to the alkane and a 42% selectivity to a mixture of dodecyl amines.

EXAMPLE II

In this example, the above experiment was repeated using an 850 cc autoclave in place of the 300 cc rotating autoclave which was used in Example I. The reaction mixture comprised 30.09 grams of undecene, 0.0282 grams of chlorodicarbonylrhodium dimer, and 0.374 grams of ammonia which was added as a 29.91 wt. % aqueous ammonia solution. After sealing the autoclave, a 1:1 mixture of carbon monoxide and hydrogen was charged to the autoclave until 150 atmospheres had been added. The mole ratio of undecene to rhodium was 1229:1 and the mole ratio of ammonia to rhodium was 156:1. The autoclave was then heated to a temperature of 150° C. and maintained in a range of from 150° to 153° C. for a period of 3 hours, the operating pressure during this period ranging from 196 to 199 atmospheres. At the end of the 3 hour period, heating was discontinued and after the autoclave had returned to room temperature, the excess pressure was discharged. The autoclave was then opened and the reaction mixture, after recovery therefrom, was analyzed by means of gas liquid chromatography. This, along with elementary analysis, showed that there had been a 100% conversion of the undecene. As in the previous example, no aldehydes were formed, but there was a 71.1% selectivity to dodecanol, a 3.4% selectivity to the alkane and a 25.5% selectivity to a mixtue of dodecyl amines.

EXAMPLE III

The above experiments were repeated using a 300 cc rotating autoclave, 0.0291 grams of chlorodicarbonylrhodium dimer, 30.05 grams of undecene and 0.383 grams of ammonia which was added as an aqueous ammonia solution. After sealing the autoclave, only 80 atmospheres of a 1:1 blend gas of carbon monoxide and hydrogen was chared to the autooclave. The autoclave was then heated to a temperature of 150° C. and maintained thereat for a period of 3 hours, the operating pressure during this period dropping from 123 atmospheres to 120 atmospheres. After recovery of the reaction mixture, analysis disclosed that there had been only a 29% conversion of the undecene with a 19.4% selectivity to dodecanol, 1.6% selectivity to the alkane and 16.1% selectivity to a mixture of dodecyl amines.

It is apparent from a comparison of Example III with Examples I and II that the higher operating pressures which are afforded by the introduction of a greater amount of blend gas will permit the higher conversion of the olefin and decrease the formation of the undesired aldehyde product.

EXAMPLE IV

To illustrate the necessity for the presence of an ammonia promoter in order to obtain an alcohol as the desired product, another experiment was performed in which 0.031 grams of chlorodicarbonylrhodium dimer and 29.96 grams of undecene were placed in the glass liner of an 850 cc rotating autoclave. After sealing the autoclave, 150 atmospheres of a 1:1 mole ratio blend gas of carbon monoxide and hydrogen was charged thereto. The mole ratio of undecene to rhodium was 1096:1. The autoclave was then heated to a temperature of 150 and maintained in a range of 150° to 153° C. for a period of 3 hours, the operating pressure during this period dropping from 211 atmospheres to 205 atmospheres. Upon completion of the reaction period, heating was discontinued and the autoclave was allowed to return to room temperature. After discharging the excess pressure, the autoclave was opened and the reaction mixture was recovered therefrom. The mixture was analyzed by means of gas liquid chromatography and elementary analysis which disclosed that there has been a 100% conversion of the undecene. However, in contradistinction to the examples which utilized an ammonia promoter, the analysis showed an 81.3% selectivity to aldehydes, dodecanol, with only a 17.8% selectivity to the alcohol, dodecanol. It is therefore readily apparent that by utilizing ammonia as a promoter for the reaction, it is possible to obtain a one-step synthesis of alcohols from olefins in which the desired product, namely the alcohol, comprises a major product which may be readily separated from any other side reaction products.

EXAMPLE V

In a manner similar to that set forth in the above examples, a mixture comprising octene, ammonia in the form of an aqueous solution, and a catalyst comprising rhodium chloride may be placed in an autoclave which is sealed. Thereafter, a blend gas of carbon monoxide and hydrogen in a 1:1 mole ratio may be charged thereto until an initial operating pressure of 150 atmospheres is reached. Thereafter, the autoclave may be heated to a temperature of about 150° C. and maintained at this temperature for a period of 3 hours; at the end of this time, heating may be discontinued and the autoclave allowed to return to room temperature. After returning to room temperature, the excess pressure may be discharged and the autoclave opened. The reaction mixture may then be subjected to gas liquid chromatography and elementary analysis to determine the presence of the desired alcohol, namely, nonanol.

In like manner, the olefins comprising heptene, docosene and butene may be subjected to a one-step synthesis reaction in the presence of ammonia and catalysts such as chlorodicarbonylrhodium dimer and rhodium chloride and also in the presence of a blend gas comprising a 1:1 mole ratio of carbon monoxide and hydrogen at operating conditions which include a pressure of about 150 atmospheres and a temperature of about 150° C. to form alcohols such as octanol, tricosanol and pentanol.

I claim as my invention:

1. In a process for the synthesis of an alcohol by the reaction of an olefinic hydrocarbon, carbon monoxide, and hydrogen in the presence of a catalyst selected from the group consisting of rhodium carbonyl compounds and rhodium-organometallic compounds, at reaction conditions, and recovering the resultant alcohol, the improvement which comprises utilizing an aqueous solution of ammonia as a promoter to produce alcohol as the major product of the process.

2. The process as set forth in claim 1 in which said reaction conditions include a temperature in the range of from about 50° to about 250° C. and a pressure in the range of from about 10 to about 300 atmospheres.

3. The process as set forth in claim 1 in which said ammonia promoter is present in said aqueous solution in an amount of about 30% by weight of said solution.

4. The process as set forth in claim 1 in which said catalyst is chlorodicarbonylrhodium dimer.

5. The process as set forth in claim 1 in which said catalyst is rhodium carbonyl.

6. The process as set forth in claim 1 in which said catalyst is chlorobis (ethylene) rhodium dimer.

7. The process as set forth in claim 1 in which said olefinic hydrocarbon is undecene and said alcohol is dodecanol.

8. The process as set forth in claim 1 in which said olefinic hydrocarbon is octene and said alcohol is nonanol.

9. The process as set forth in claim 1 in which said olefinic hydrocarbon is heptene and said alcohol is octanol.

10. The process as set forth in claim 1 in which said olefinic hydrocarbon is docosene and said alcohol is tricosanol.

11. The process as set forth in claim 1 in which said olefinic hydrocarbon is butene and said alcohol is pentanol.

* * * * *